(12) United States Patent
Otake et al.

(10) Patent No.: US 6,951,175 B2
(45) Date of Patent: Oct. 4, 2005

(54) METHOD FOR FORMING PRINTING INSPECTION DATA

(75) Inventors: Yuji Otake, Fukuoka (JP); Takahiro Fukagawa, Ogouri (JP); Takashi Katsuki, Chikushino (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 95 days.

(21) Appl. No.: 10/642,930

(22) Filed: Aug. 18, 2003

(65) Prior Publication Data

US 2004/0031406 A1    Feb. 19, 2004

(30) Foreign Application Priority Data

Aug. 19, 2002 (JP) ........................ P. 2002-238088
Aug. 19, 2002 (JP) ........................ P. 2002-238089

(51) Int. Cl.[7] ............................................ B41F 21/12
(52) U.S. Cl. ...................... 101/485; 101/129; 101/484
(58) Field of Search ................................ 101/485, 129, 101/484

(56) References Cited

U.S. PATENT DOCUMENTS

| | | | |
|---|---|---|---|
| 5,450,204 A * | 9/1995 | Shigeyama et al. | ......... 356/604 |
| 5,912,984 A | 6/1999 | Michael et al. | |
| 5,991,435 A * | 11/1999 | Tsujikawa et al. | ......... 382/147 |
| 6,088,109 A * | 7/2000 | Liu | ............. 356/602 |
| 6,167,149 A * | 12/2000 | Tsujikawa et al. | ......... 382/147 |
| 6,634,290 B1 * | 10/2003 | Shimizu et al. | ............. 101/219 |
| 6,665,066 B2 * | 12/2003 | Nair et al. | ................. 356/237.2 |
| 6,750,899 B1 * | 6/2004 | Fishbaine et al. | ............ 348/126 |

FOREIGN PATENT DOCUMENTS

| | | |
|---|---|---|
| DE | 197 28 144 A1 | 1/1997 |
| EP | 0563829 A2 * | 10/1993 ......... G01R 31/308 |
| EP | 1 048 946 A2 | 11/2000 |
| JP | 2002029033 | 1/2002 |

OTHER PUBLICATIONS

Patent Abstracts of Japan, Sakaguchi Hiroyuki, "Apparatus and Method for Visual Inspection of Cream Solder", Publication No.: 11186711, Publication Date Jul. 9, 1999, 1 page.

* cited by examiner

Primary Examiner—Charles H. Nolan, Jr.
(74) Attorney, Agent, or Firm—Pearne & Gordon LLP

(57) ABSTRACT

It is an object of the invention to provide a method for forming printing inspection data in which the use of a mask plate makes it possible to simply and efficiently form the inspecting data.

In a method for forming printing inspection data for obtaining mask opening data from an image got by picking-up the image of a mask plate to form the inspecting data, when an image pick-up visual field 20a is sequentially moved to visual field positions having a grid-shaped arrangement to obtain a plurality of images, if incomplete opening parts 16b (X) and (Y) in which parts of the opening parts protrude are detected, ranges BX2 and BY2 which are excluded from an object of data in this image are determined based on these sizes BY1 and BY2. When the image pick-up visual field is moved to an adjacent visual field position, the image pick-up visual field is overlapped on the adjacent image pick-up visual field by BX2, BY2 to include these opening parts in the adjacent image pick-up visual field. Thus, an inconvenience that the opening parts protrude in the image is eliminated so that the inspecting data can be simply and efficiently formed.

7 Claims, 16 Drawing Sheets

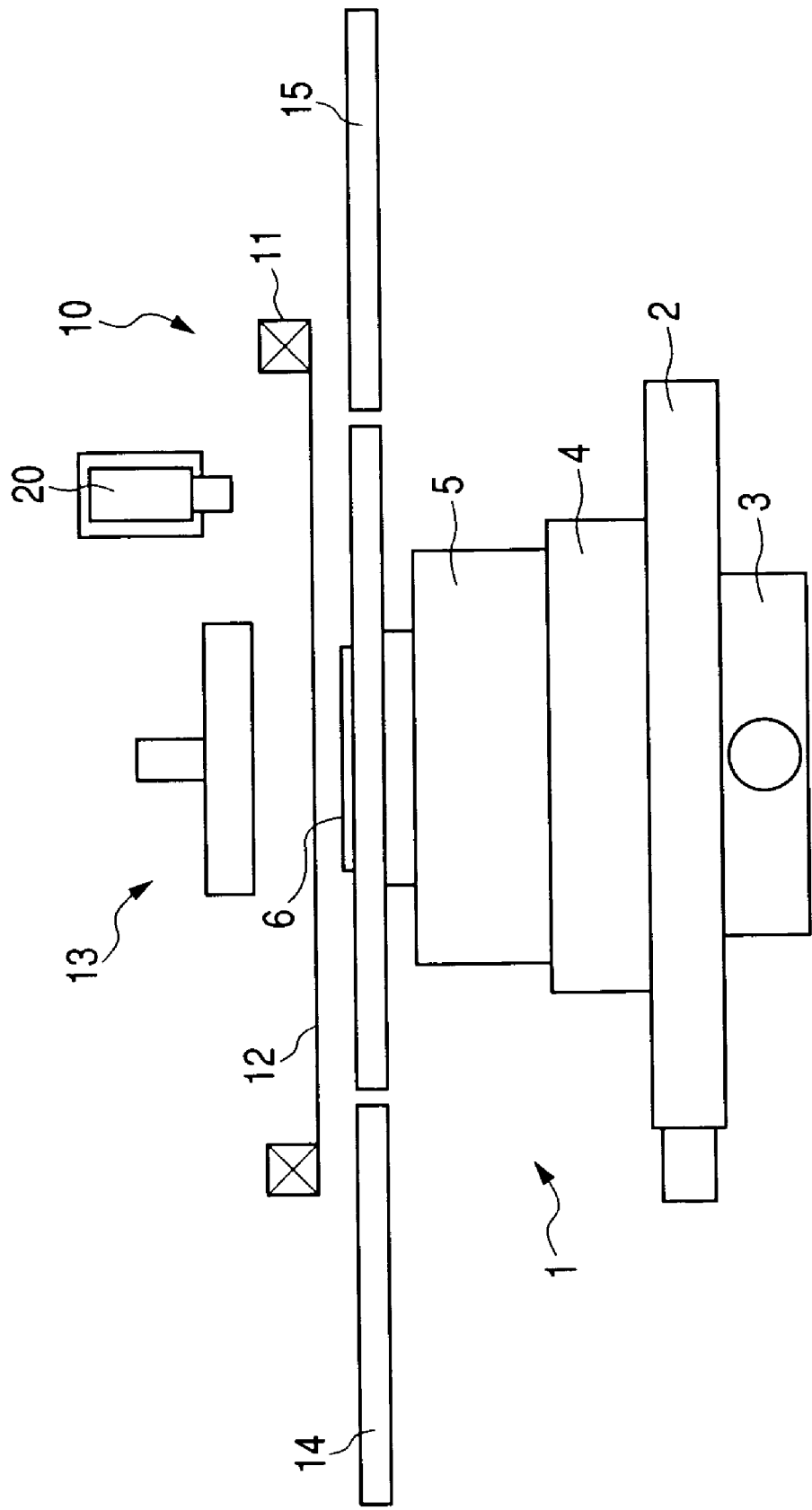

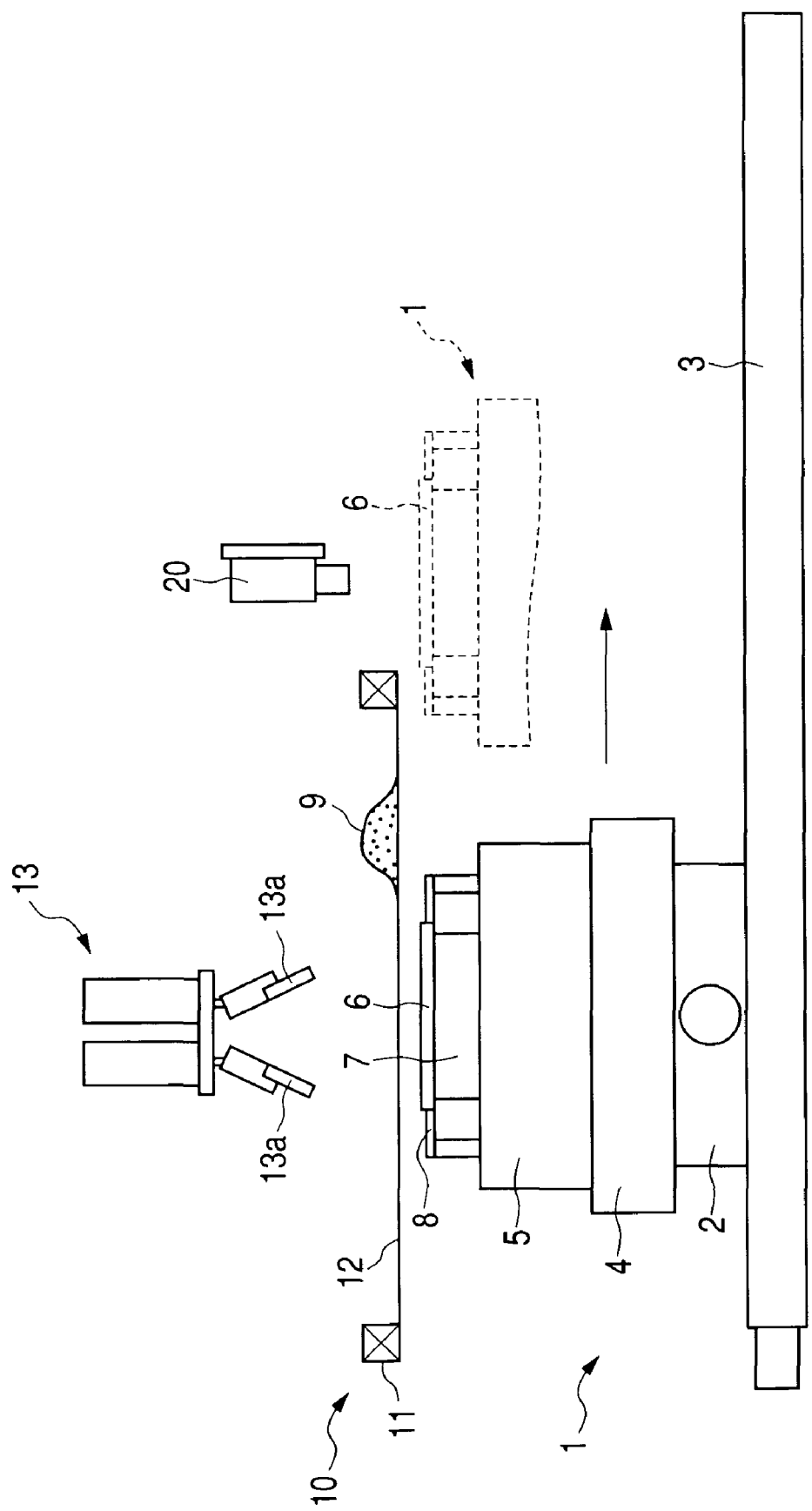

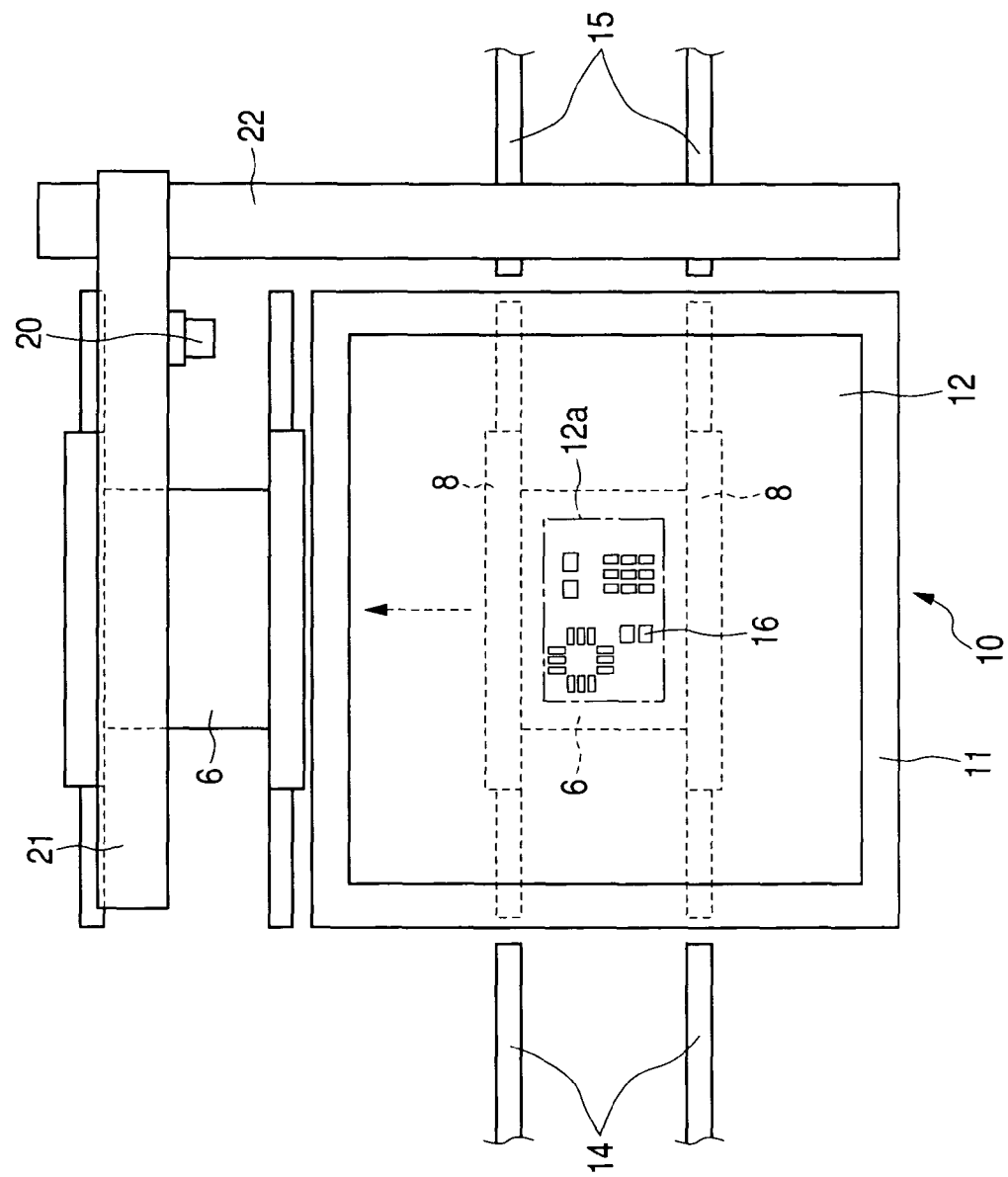

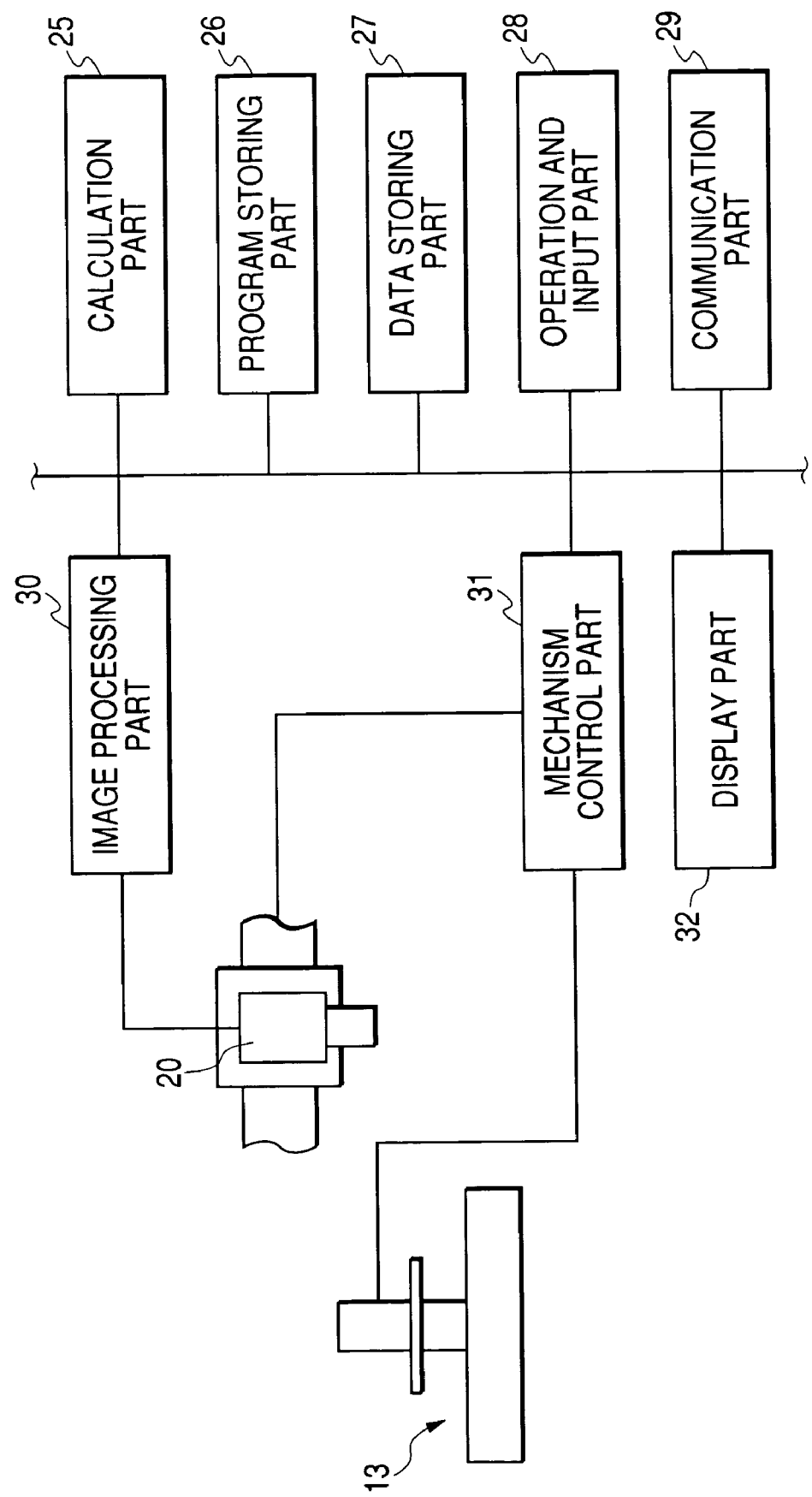

METHOD FOR FORMING PRINTING INSPECTION DATA

BACKGROUND OF THE INVENTION

1. Field of the Invention

The present invention relates to a method for forming printing inspection data used in a printing inspection apparatus for inspecting the printed state of a cream solder printed on a board.

2. Description of the Related Art

In mounting electronic parts, cream solder is applied to the surface of a board before the electronic parts are mounted on the board. As a method for applying the cream solder, a screen printing method is widely employed. After a printing step, a printing inspection for inspecting the printed state of the cream solder is carried out. This printing inspection decides whether or not the cream solder is properly printed on a printing position by picking-up the image of the board after the screen printing by a camera and processing the image of the picked-up result. Then, before the printing inspection, inspecting data for instructing the printing position on which the cream solder of the board to be inspected is printed is inputted to a printing inspection apparatus.

The inspecting data has been hitherto formed by various kinds of methods. For example, a variety of kinds of methods include a method of using mask data showing the forms of pattern holes of a mask plate used for printing, a method of obtaining electrode positions from the mounting data of a board, a method of obtaining these data from an actual mask plate used for printing, etc. The method for using the mask plate of these methods serves to detect the opening positions or the forms of the pattern holes by a method of recognizing images or the like. In this method, the inspecting data can be advantageously formed on the spot of production even when the mask data or the mounting data is not given.

However, the method of using the mask plate has problems as described below. When the opening parts of the mask plate are detected by recognizing the images, the image pick-up visual field of a camera used for picking-up images is ordinarily smaller than the size of the mask plate. In order to recognize an image, the image needs to be picked up a plurality of times while the image pick-up visual field of the camera is moved on the mask plate. Then, recognized results obtained by a plurality of images are combined together to detect the position or the form of each opening part on the mask plate.

However, at this time, each opening part is not necessarily incorporated in any of the image pick-up visual fields in a complete form, and the opening parts may sometimes partly protrude from one image pick-up visual field. In such a case, it has been hitherto difficult to precisely obtain the positions or the forms of the opening parts, so that the simple and efficient formation of the inspecting data using the mask plate has been prevented.

SUMMARY OF THE INVENTION

Accordingly, it is an object of the present invention to provide a method for forming printing inspection data in which the inspecting data can be simply and efficiently formed by using a mask plate.

A first aspect of the invention provides a method for forming printing inspection data which is used in a printing inspection apparatus for inspecting the printed state of the cream solder of a board after a screen printing to form the inspecting data including configuration and position data showing the configurations and positions of solder printing parts in which the cream solder is printed on a printing surface, wherein, in a mask data obtaining step for obtaining element configuration and position data showing the configurations and the positions of the element solder printing parts printed on electrodes for connecting together electronic parts provided on the circuit forming surface of the board by detecting opening parts of a mask plate on the basis of images obtained by picking-up the images of the mask plate used for the screen printing by a camera, when the image pick-up visual field of the camera is sequentially moved to a plurality of visual field positions set to the mask plate in accordance with a prescribed moving sequence to obtain a plurality of images, if an incomplete opening part in which a part of the opening part partly protrudes so that a configuration is not completed is detected from an image obtained in one image pick-up visual field, a process for obtaining a complete opening part to which the incomplete opening part belongs is carried out in accordance with the detected result.

A second aspect of the invention provides a method for forming printing inspection data which is used in a printing inspection apparatus for inspecting the printed state of the cream solder of a board after a screen printing to form the inspecting data including configuration and position data showing the configurations and positions of solder printing parts in which the cream solder is printed on a printing surface, wherein, in a mask data obtaining step for obtaining element configuration and position data showing the configurations and the positions of element solder printing parts printed on electrodes for connecting together electronic parts provided on the circuit forming surface of the board by detecting opening parts of a mask plate on the basis of images obtained by picking-up the images of the mask plate used for the screen printing by a camera, when the image pick-up visual field of the camera is sequentially moved to a plurality of visual field positions set to the mask plate in accordance with a prescribed moving sequence to obtain a plurality of images, if an incomplete opening part in which a part of the opening part partly protrudes so that a configuration is not completed is detected from an image obtained in one image pick-up visual field, an adjacent image pick-up visual field in the end of the image in which the incomplete opening part is detected is overlapped on the one image pick-up visual field by an overlap margin determined by the size of the incomplete opening part in the image.

A third aspect of the invention provides a method for forming printing inspection data according to the second aspect, wherein the plural visual field positions are set in a substantially grid shaped arrangement and the prescribed moving sequence is a moving sequence performed in such a manner that a liner column movement toward the same direction from a start end to a terminal end in a first direction in the grid shaped arrangement is repeated in a second direction perpendicular to the first direction.

A fourth aspect of the invention provides a method for forming printing inspection data according to the third aspect, wherein the overlap margin in the second direction of the overlap margins in which two adjacent image visual fields are overlapped in the second direction is set on the basis of a maximum size of sizes of the incomplete opening parts in the second direction which are detected in the first column movement and the same overlap margin in the second direction is used in a column movement subsequent to the first column movement.

A fifth aspect of the invention provides a method for forming printing inspection data which is used in a printing inspection apparatus for inspecting the printed state of the cream solder of a board after a screen printing to form the inspecting data including configuration and position data showing the configurations and positions of solder printing parts in which the cream solder is printed on a printing surface, wherein, in a mask data obtaining step for obtaining element configuration and position data showing the configurations and the positions of element solder printing parts printed on electrodes for connecting together electronic parts provided on the circuit forming surface of the board by detecting opening parts of a mask plate on the basis of images obtained by picking-up the image of the mask plate used for the screen printing by a camera, when the image pick-up visual field of the camera is sequentially moved to a plurality of visual field positions set to the mask plate in accordance with a prescribed moving sequence to obtain a plurality of images, if an incomplete opening part in which a part of the opening part partly protrudes so that a configuration is not completed is detected from an image obtained in one image pick-up visual field, the incomplete opening part is registered as an opening part to be connected in the image, and then, a connecting process is carried out in which an opening part to be connected that is already registered in an image obtained in an adjacent image pick-up visual field on the edge of the image edge where the opening part to be connected is detected and corresponds to the opening part to be connected is connected to the opening part to be connected to form one opening part.

A sixth aspect of the invention provides a method for forming printing inspection data according to the fifth aspect, wherein the plural visual field positions are set in a substantially grid shaped arrangement and the prescribed moving sequence is a moving sequence performed in such a manner that a liner column movement toward the same direction from a start end to a terminal end in a first direction in the grid shaped arrangement is repeated in a second direction perpendicular to the first direction.

A seventh aspect of the invention provides a method for forming printing inspection data according to the sixth aspect, wherein when the opening part to be connected is dislocated from the already-registered opening part to be connected in the connecting process, both the opening parts are respectively moved by half an amount of dislocation toward the central point of dislocation.

According to one of the aspects of the invention, in the mask data obtaining step for obtaining the positions or the configurations of the opening parts by picking-up the image of the mask plate, when the image pick-up visual field of the camera is sequentially moved to a plurality of visual field positions set to the mask plate in a prescribed moving sequence, if the incomplete opening parts partly protruding from the image obtained in one image pick-up visual field are detected, a process for obtaining the complete opening parts to which the incomplete opening parts belong is performed based on the detected result. Therefore, the inspecting data can be simply and efficiently formed.

According to one of the aspects of the invention, in the mask data obtaining step for picking-up the image of the mask plate to obtain the positions or the forms of the opening parts, when the image pick-up visual field of the camera is sequentially moved to the plural visual field positions set to the mask plate in accordance with a prescribed moving sequence, if the incomplete opening parts which partly protrude from the image obtained in one image pick-up visual field are detected, the adjacent image pick-up visual field is overlapped by the overlap margin determined based on the size of the incomplete opening parts in the image on the one image pick-up visual field to pick-up the image. Thus, an inconvenience due to the protrusion of the opening parts in the obtained image can be eliminated and the inspecting data can be simply and efficiently formed.

According to one of the aspects of the invention, in the mask data obtaining step for obtaining the positions or the configurations of the opening parts by picking-up the image of the mask plate, when the image pick-up visual field of the camera is sequentially moved to a plurality of visual field positions set to the mask plate in a prescribed moving sequence, if the incomplete opening parts partly protruding from the image obtained in one image pick-up visual field are detected, the incomplete opening parts are registered as the opening parts to be connected in this image, and then, a connecting process is carried out in which the opening parts to be connected that are already registered in the image obtained in the adjacent image pick-up visual filed in the edge of the image in which the opening parts to be connected are detected and correspond to the opening parts to be connected are connected to the opening parts to be connected to form complete openings respectively. Accordingly, the inspecting data can be simply and efficiently formed.

BRIEF DESCRIPTION OF THE DRAWINGS

FIG. 1 is a front view of a screen-printing apparatus according to a first embodiment.

FIG. 2 is a side view of the screen-printing apparatus according to the first embodiment of the present invention.

FIG. 3 is a plan view of the screen-printing apparatus according to the first embodiment of the present invention.

FIG. 5 is a block diagram showing the structure of a control system of the screen-printing apparatus according to the first embodiment of the present invention.

DESCRIPTION OF THE PREFERRED EMBODIMENTS (First Embodiment)

In the present invention according to a first embodiment, in a mask data obtaining step for obtaining positions or forms of opening parts by picking-up the image of a mask plate, when the image pick-up visual field of a camera is sequentially moved to a plurality of visual field positions set to the mask plate in accordance with a prescribed moving sequence, if incomplete opening parts partly protruding from an image obtained in one image pick-up visual field are detected, an adjacent image pick-up visual field is overlapped on the one image pick-up visual field by an overlap margin determined by the sizes of the incomplete opening parts in the image. Thus, an inconvenience that the opening parts protrude in the obtained image is eliminated so that inspecting data can be simply and efficiently formed.

Figure 6:
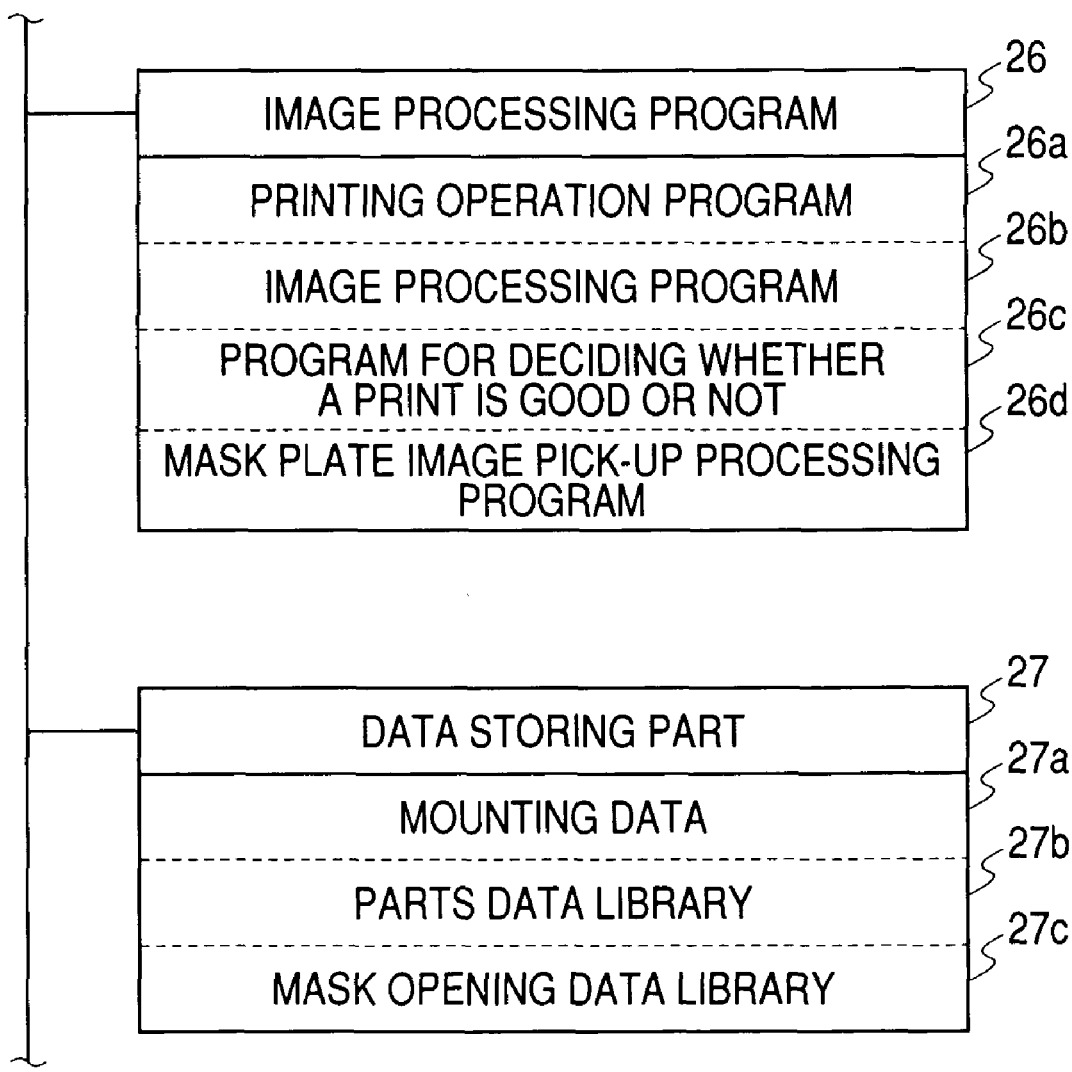
FIG. 6 is a view showing the storage contents of a program storing part and a data storing part of the screen-printing apparatus according to the first embodiment of the present invention.
Figure 7:
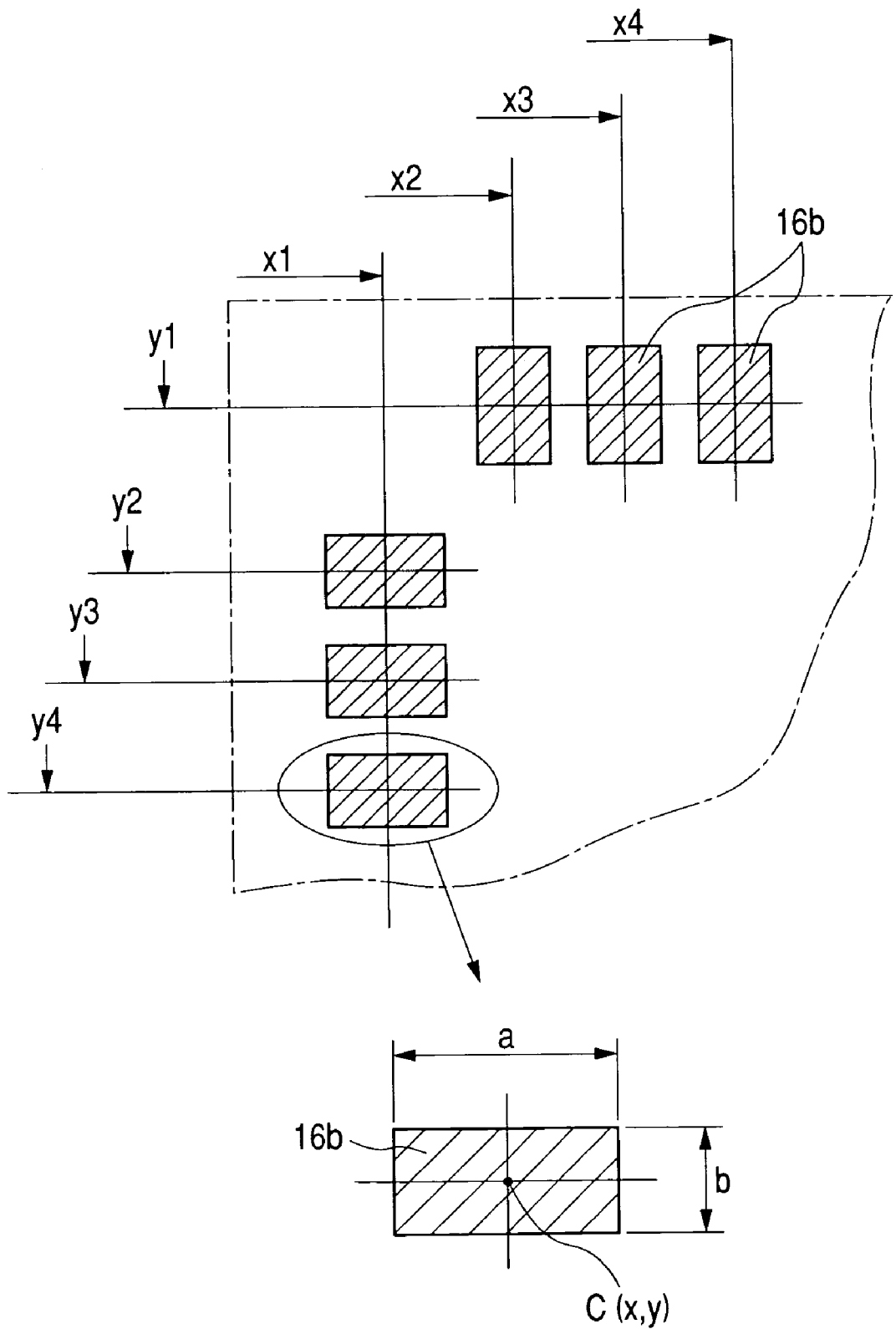
FIG. 7 is an explanatory view of element form and position data of element solder printing parts of the screen-printing apparatus according to the first embodiment of the present invention.
Figure 8:
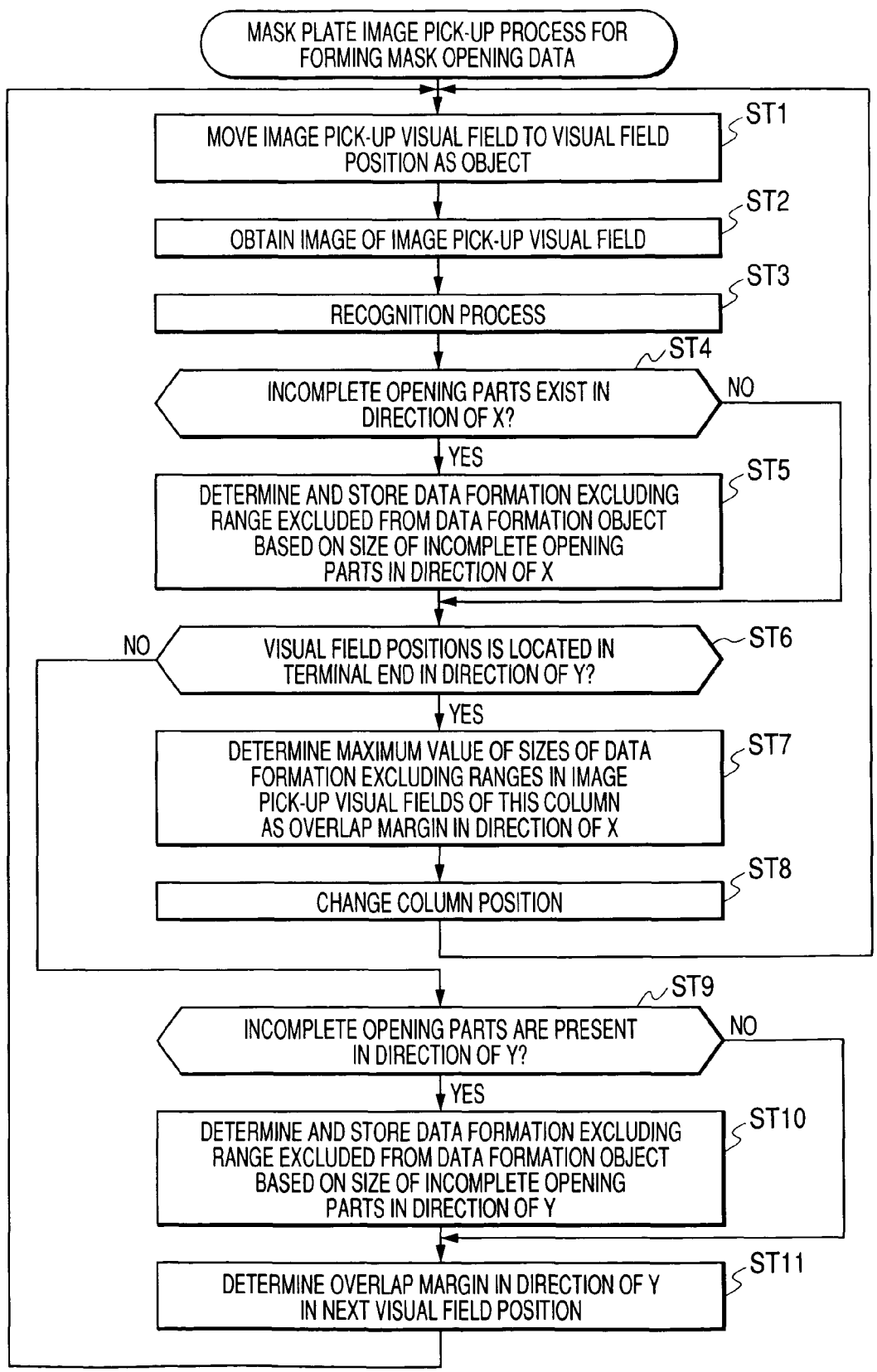
FIG. 8 is a flow chart for a mask plate image pick-up process for forming mask opening data in a method for forming print inspecting data according to the first embodiment of the present invention.
Figure 9:
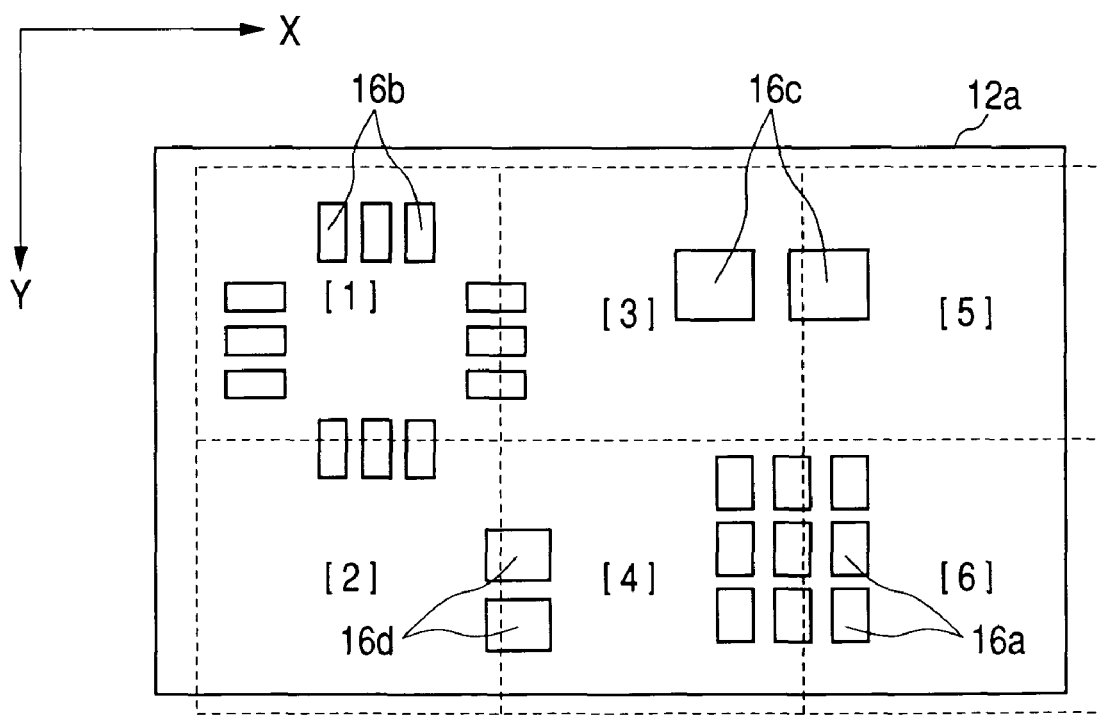
FIG. 9 is a diagram showing visual field positions upon mask plate image pick-up process in the method for forming print inspecting data according to the first embodiment of the present invention.

Now, the embodiment of the present invention will be described by referring to the drawings. FIG. 1 is a front view of a screen-printing apparatus according to a first embodiment. FIG. 2 is a side view of the screen-printing apparatus according to the first embodiment of the present invention. FIG. 3 is a plan view of the screen-printing apparatus according to the first embodiment of the present invention. FIG. 4 is a plan view of a board printing surface by the screen-printing apparatus according to the first embodiment of the present invention. FIG. 5 is a block diagram showing the structure of a control system of the screen-printing apparatus according to the first embodiment of the present invention. FIG. 6 is a view showing the storage contents of a program storing part and a data storing part of the screen-printing apparatus according to the first embodiment of the present invention. FIG. 7 is an explanatory view of element form and position data of element solder printing parts of the screen-printing apparatus according to the first embodiment of the present invention. FIG. 8 is a flow chart for a mask plate image pick-up process for forming mask opening data in a method for forming printing inspection data according to the first embodiment of the present invention. FIG. 9 is a diagram showing a visual field position upon mask plate image pick-up process in the method for forming printing inspection data according to the first embodiment of the present invention. FIGS. 10, 11 and 12 are explanatory views of the mask plate image pick-up process in the method for forming printing inspection data according to the first embodiment of the present invention.

Initially, the structure of the screen-printing apparatus will be described with reference to FIGS. 1, 2 and 3. The screen-printing apparatus has a structure including not only a printing mechanism for printing cream solder on a board on which electronic parts are mounted, but also a function as a printing inspection apparatus for inspecting the printed state of the scream solder on the board after a screen printing, and a function in a printing inspection, as described below, as a printing inspection data forming apparatus for forming inspecting data including form and position data indicating the forms and the positions of solder printing parts on which the cream solder is printed.

In FIGS. 1 and 2, a board positioning part 1 comprises a θ-axis table 4 stacked on a moving table including an X-axis table 2 and a Y-axis table 3 and a Z-axis table 5 further disposed thereon. On the Z-axis table 5, a board holding part 7 for holding a board 6 held by a damper 8 from a lower part is provided. The board 6 as an object to be printed is conveyed to the board positioning part 1 by a take-in conveyor 14 shown in FIGS. 1 and 3. The board positioning part 1 is driven so that the board 6 is moved to X and Y directions and positioned at a below-described printing position and a board recognizing position. A take-out conveyor 15 conveys out the board 6 after the printing operation.

Figure 4A:
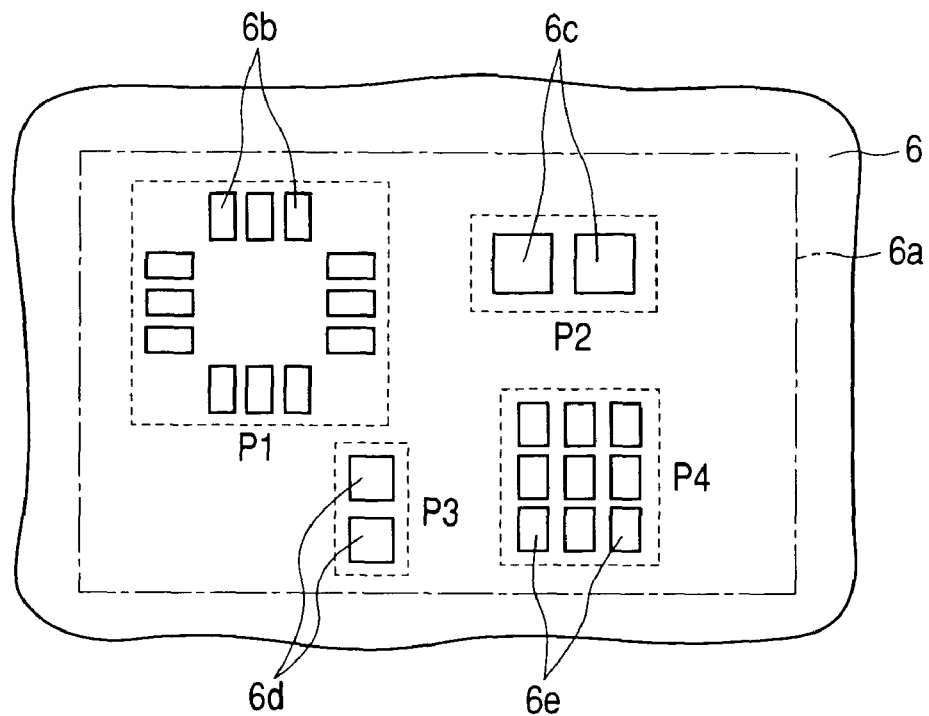
FIG. 4 is a plan view of a board printing surface by the screen-printing apparatus according to the first embodiment of the present invention.

Above the board positioning part 1, a screen mask 10 is arranged. A mask plate 12 is mounted on a holder 11 to form the screen mask 10. The board 6 is positioned and abuts on the mask plate 12 from a lower part by the board positioning part 1. Within a solder printing range 6a on a circuit forming surface of the board 6, electrodes 6b, 6c, 6d and 6e for connecting together different kinds of electronic parts P1, P2, P3 and P4 are provided as shown in FIG. 4(a).

Figure 4B:
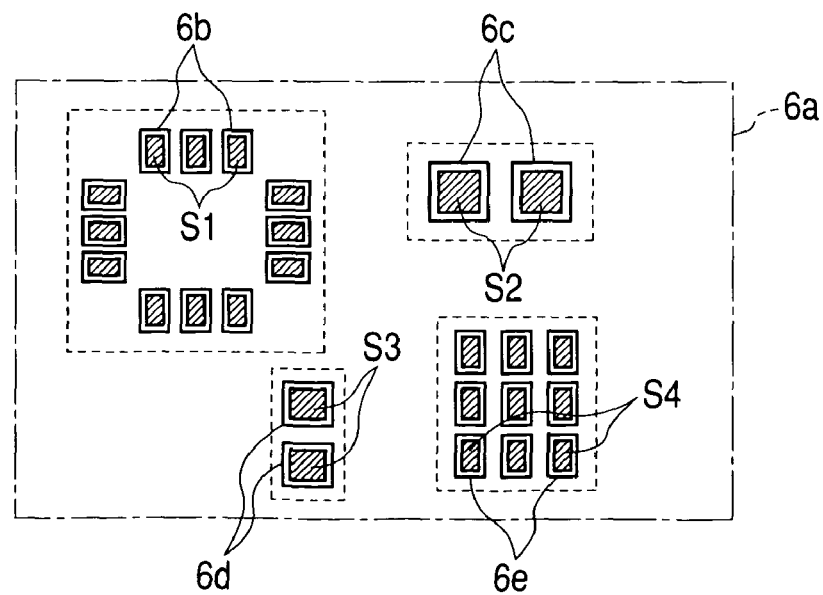

On the screen mask 10, a squeegee head 13 is arranged to freely reciprocate in the horizontal direction. While the board 6 abuts on the lower surface of the mask plate 12, cream solder 9 is supplied onto the mask plate 12 and the squeegees 13a of the squeegee head 13 are allowed to abut and slide on the surface of the mask plate 12, so that the cream solder 9 is printed on the printing surface of the board 6 through pattern holes 16 provided on the mask plate 12. Thus, as shown in FIG. 4(b), element solder printing parts S1, S2, S3 and S4 are respectively formed on the electrodes 6b, 6c, 6d and 6e.

Above the screen mask 10, a camera 20 as image pick-up means is provided. As shown in FIG. 3, the camera 20 is horizontally moved in X and Y directions by an X-axis table 21 and a Y-axis table 22. The X-axis table 21 and the Y-axis table 22 are camera moving means for moving the camera 20. The camera 20 is moved relative to the mask plate 12 by the camera moving means so that the camera 20 picks-up the images of arbitrary positions of the mask plate 12.

As shown in FIG. 2, the board positioning part 1 is moved in a Y direction from a lower part of the screen mask 10 by the Y-axis table 3 to move the held board 6 to a board recognizing position. Under this state, the camera 20 is moved to the board 6 on the board positioning part 1 so that the camera 20 can pick-up the images of the arbitrary positions of the board 6.

Now, referring to FIG. 5, the structure of a control system of a screen printing apparatus will be described below. In FIG. 5, a calculation part 25 is a CPU to perform various kinds of programs stored in a program storing part 26 so that the calculation part 25 performs various kinds of calculations and processes described below. In these calculations and processes, various types of data stored in a data storing part 27 are employed.

An operation and input part 28 is input means such as a keyboard or a mouse to input various kinds of control commands or data. A communication part 29 transmits data to and receives data from other apparatus forming electronic parts mounting line together with the screen printing apparatus. An image processing part 30 performs an image process of image data picked-up by the camera 20 to recognize solder printing parts for a printing inspection or detect mask opening parts for forming printing inspection data, as described below.

A mechanism control part 31 controls the camera moving means for moving the camera 20 or squeegee moving means for moving the squeegee head 13. A display part 32 is a display apparatus and serves as display means for displaying an operating screen in a printing inspection data forming process or the decided result of the print inspection as well as images obtained by the camera 20.

Now, referring to FIG. 6, the programs and the data respectively stored in the program storing part 26 and the data storing part 27 will be described. In the program storing part 26, the various kinds of programs including a printing operation program 26a, an image processing program 26b, a program 26c for deciding whether a print is good or not, a mask plate image pick-up processing program 26d or the like are stored.

The printing operation program 26a is a program for the printing operation for controlling the operations of the board positioning part 1 and the squeegee head 13 to print the cream solder 9 on the board 6. The image processing program 26b is a program according to which the image processing part 30 carries out two kinds of processes described below based on the image pick-up results of the camera 20.

Firstly, the image pick-up result obtained by picking-up the image of the board 6 after printing is recognized to detect the element solder printing parts (see FIG. 4(b)) respectively formed on the electrodes of the board 6 and calculate the area of each element solder printing part. Further, the image pick-up result obtained by picking-up the image of the mask plate 12 is recognized to detect each pattern hole 16 provided in the mask plate 12 and form mask opening data based on the detected result.

The program 26c for deciding whether a print is good or not compares the area of the element solder printing part calculated by the image processing part 30 with an inspection threshold value to decide whether or not the printed state of each element solder printing part is good. That is, a function realized by the image processing part 30 and the calculation part 25 which perform the program 26c for deciding whether a print is good or not constitutes print deciding means for deciding whether a printed state is good or not on the basis of the image pick-up result of the board and the inspecting data necessary for performing the printing inspection.

The mask plate image pick-up processing program 26d is a program for performing a necessary process when the mask plate 12 is divided by a plurality of image pick-up visual fields to pick-up images upon picking-up the image of the mask plate 12 by the camera 20 to prepare the mask opening data. As described below, opening parts showing the pattern holes are prevented from being divided by the boundaries of the image pick-up visual fields by this mask plate image pick-up process.

In the data storing part 27, mounting data 27a, a parts data library 27b and a mask opening data library 27c are stored. The mounting data 27a, the parts data library 27b and the mask opening data library 27c of these data are transferred from other apparatus such as data managing computer through a communication part 29 and stored.

The mounting data 27a is data used in a mounting operation for mounting electronic parts on the board on which the cream solder is printed, that is, data in which the kinds of electronic parts to be mounted are associated with mounting position coordinates on the board. The parts data library 27b is data related to individual electronic parts to be mounted on the board. The mask opening data library 27c stores numeric value data showing the opening positions or the sizes of the pattern holes 16 of the mask plate 12 used for printing for many kinds of goods and is previously given as the mask opening data attached to the individual mask plates.

In an example of the mask plate 12 shown in FIG. 7, data of each pattern hole 16b or 16e is given. For instance, as for the pattern hole 16b, dimensions a and b showing the size of the pattern hole or the position coordinate values x1, x2, x3, x4 . . . , y1, y2, y3, y4 . . . of each pattern hole 16b relative to a reference origin are given in the form of numeric value data. As for other pattern holes, the same data is given. This mask opening data is used as element position and form data showing the positions and forms of the element solder printing parts (S1 to S4) shown in FIG. 4(b) in the print inspection.

When an inspection after the printing operation is performed, the mask opening data is not necessarily prepared as data library for all kinds of boards so that a performer side of the inspection may sometimes need to prepare the mask opening data. In this case, as described above, the image of the actual mask plate 12 is picked-up by the camera 20 to form the mask opening data.

That is, upon forming the printing inspection data in such a case, a process for obtaining element form and position data (a mask data obtaining step), is carried out, which shows the forms and positions of the element solder printing parts printed on the electrodes for connecting electronic parts provided on the circuit forming surface of the board by detecting the opening parts of the mask plate based on the images got by picking-up the image of the mask plate used for the screen printing by the camera.

Subsequently, a mask plate image pick-up process for forming the mask opening data will be described by referring to each figure. Firstly, referring to FIG. 9, the arrangement of visual field positions set to the mask plate 12 is described. Ordinarily, the printing range of the mask plate 12 whose image is to be picked-up is larger than the image pick-up visual field of the camera 20. Accordingly, when the image of one mask plate is picked-up, the image needs to be picked-up a plurality of times while the position of the image pick-up visual field of the camera 20 is sequentially shifted. Therefore, when the image of the mask plate is picked-up, visual field positions as target positions where the image pick-up visual field moves are previously set to the mask plate on the basis of a visual field size.

Specifically, as shown in FIG. 9, to a printing range 12a, a plurality of visual field positions [1], [2], [3], [4], [5] and [6] are set in a grid shaped arrangement having two rows and three columns. That is, the visual field positions are set in the grid shaped arrangement having rows combined with columns. In this arrangement, [1] and [2] form a first column, [3] and [4] form a second column and [5] and [6] form a third column. Then, the image pick-up visual field 20a of the camera 20 is sequentially moved to these visual field positions in a prescribed moving sequence to obtain a plurality of images. Accordingly, a necessary image pick-up range can be completely covered.

Here, as described below, the prescribed moving sequence is a moving sequence performed in such a manner that a linear column movement (from an upper side to a lower side in FIG. 9) toward the same direction from a start end side to a terminal end side of a first direction (Y direction) in the grid-shaped arrangement is repeated for each column in a second direction (X direction) perpendicular to the first direction.

Here, grid shaped broken lines show visual field boundaries when the image pick-up visual filed 20a of the camera 20 is located in these visual fields. When the visual field positions are set as shown in FIG. 9, the visual field boundaries may sometimes traverse the pattern holes. This means a fact that when the image pick-up visual field is simply moved to these visual field positions to pick-up the image, an opening part showing one pattern hole is detected over a plurality of images.

In the opening part divided and included in the plural images as described above, the position or the form of the opening part cannot be obtained under this state. Accordingly, in this embodiment, the positions or the forms of the opening parts to which incomplete opening parts detected in their divided forms belong are obtained by a method described below.

Figure 10A:
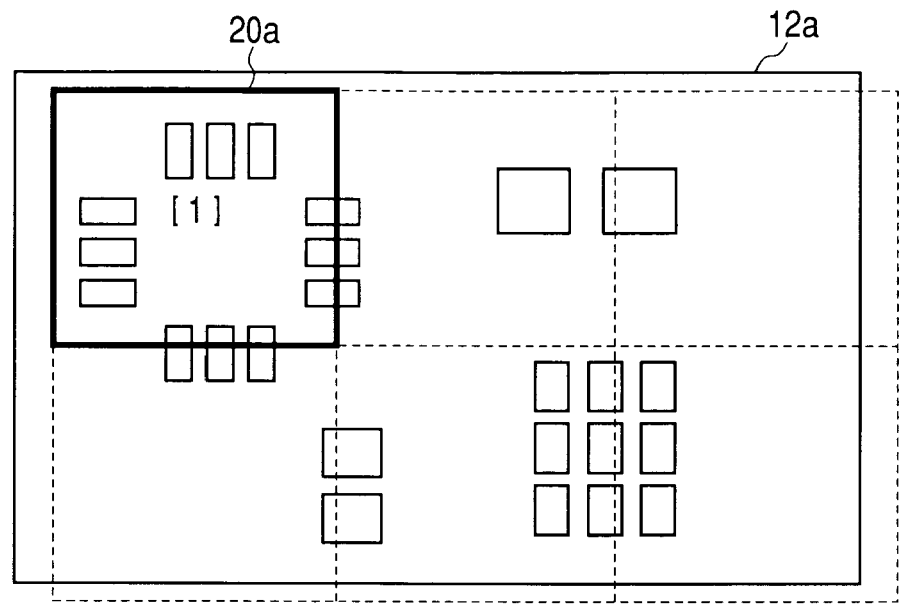
FIG. 10 is an explanatory view of the mask plate image pick-up process in the method for forming print inspecting data according to the first embodiment of the present invention.

Now, a specific image pick-up process will be described in accordance with a flow chart of FIG. 8. Firstly, the camera 20 is moved on the mask plate 12 to move the image pick-up visual field 20a to a target visual field position (ST1). Here, as shown in FIG. 10(a), the first visual field position [1] is a first object whose image is to be picked-up. Then, the image of this image pick-up visual field is obtained by the camera 20 (ST2) to recognize the obtained image (ST3). Thus, an image 20b shown in FIG. 10(b) is obtained and the pattern holes 16b in the image pick-up visual field are detected as the opening parts.

Here, it is decided whether or not the incomplete opening parts in which parts of the opening parts partly protrude from the image 20b so that the forms are not completed are detected in a direction of X (ST4). Then, when the incomplete opening parts are present in the direction of X, a data formation excluding range which is excluded from a range where data is to be formed is determined based on the sizes of the detected incomplete opening parts in the direction of X and stored (ST5).

Figure 10B:
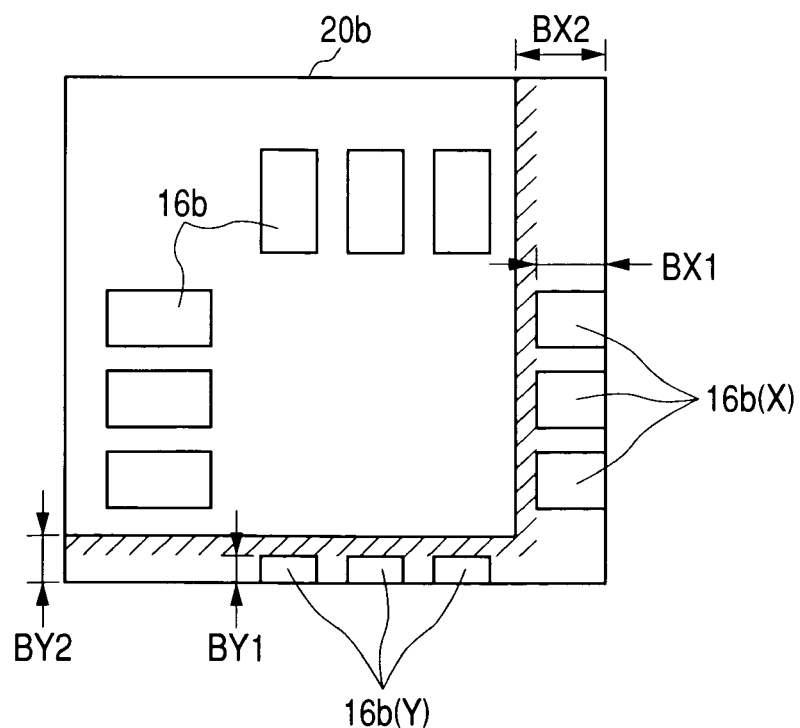

Specifically, in this example, as shown in FIG. 10(b), incomplete opening parts 16b (X) corresponding to the pattern holes 16b are detected in the right boundary side in the image 20b. Then, the size BX1 of the incomplete opening part 16b (X) in the direction of X is obtained on the image. The range of a width size BX2 obtained by adding a prescribed margin to the BX1 is considered to be the data formation excluding range (see oblique line hatching parts). The part considered to be the data formation excluding range as described above is not a part for which the mask opening data is to be formed in the image. As described below, such a visual field movement as to include these incomplete opening parts in an adjacent image pick-up visual field is carried out.

Then, it is decided whether or not the above-described visual field position is located in a terminal end in the direction of Y (ST6). Since the visual field position [1] is not located in the terminal end in the direction of Y, the procedure advances to (ST9) to decide whether or not incomplete opening parts are present in the direction of Y. Then, when the incomplete opening parts are present in the direction of Y, a data formation excluding range which is excluded from a range where data is to be formed is determined based on the size of the detected incomplete opening parts in the direction of Y and stored (ST10).

In the example shown in FIG. 9(b), incomplete opening parts 16b (Y) are detected in the lower boundary side in the image 20b. The size BY1 of the detected incomplete opening parts 16b (Y) in the direction of Y is obtained on the image. The range of a width size BY2 obtained by adding a prescribed margin to the BY1 is considered to be a data formation excluding range (see oblique line hatching parts).

Figure 11A:
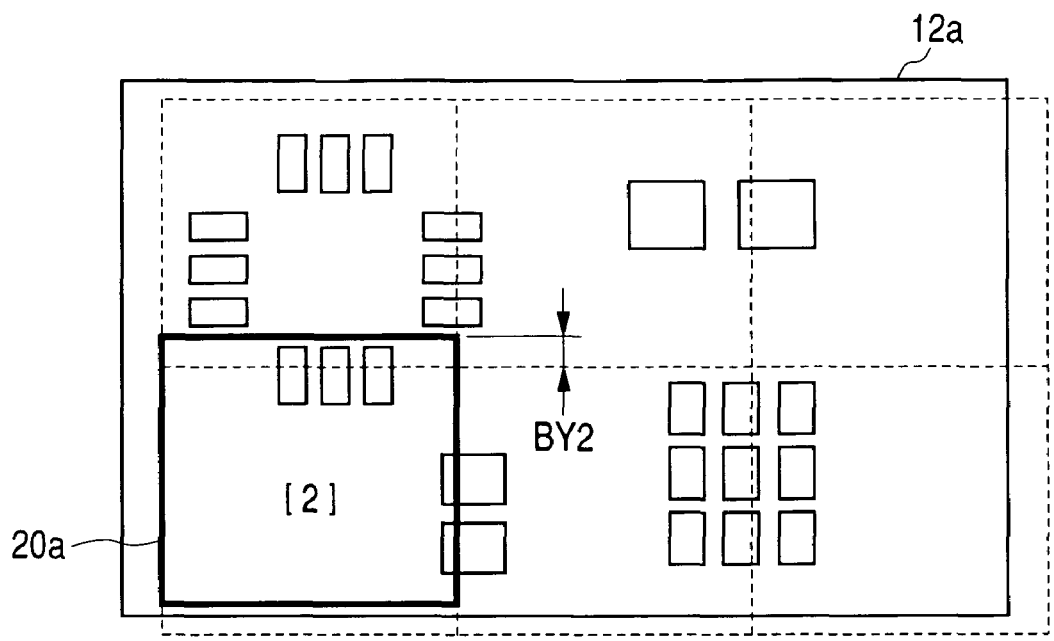
FIG. 11 is an explanatory view of the mask plate image pick-up process in the method for forming print inspecting data according to the first embodiment of the present invention.

Then, when the data formation excluding range in the direction of Y is determined, the width size BY2 is determined to be an overlap margin in the direction Y in a next visual field (ST11) and the procedure returns to (ST1). As shown in FIG. 11(a), the image pick-up visual field 20a is moved to the visual field position [2] as a next object. At this time, as for an amount of movement of the visual field 20a, the visual field 20a is not directly moved by a visual field size in the direction of Y, and the visual field 20a is overlapped by the BY2 determined as the overlap margin in the direction of Y on the image pick-up visual field in the previous visual field position. That is, the overlap margin in the direction of Y is determined based on the size of the incomplete opening parts in the direction of Y in the image.

Figure 11B:
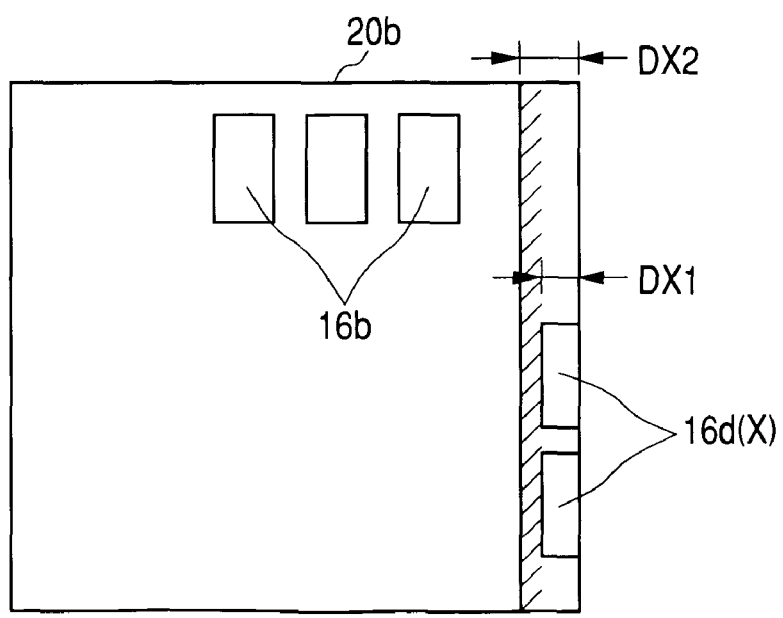

Thus, as shown in FIG. 11(b), the image 20b in which the pattern holes 16b, which are the incomplete opening parts on the image obtained in the visual field position [1], are completely included is obtained. Then, the same processes are performed on the image 20b. Here, incomplete opening parts 16d (X) corresponding to pattern holes 16d are detected in the right boundary side in the image 20b. Then, the size DX1 of the incomplete opening parts 16d (X) in the direction of X is obtained on the image. The range of a width size DX2 is likewise determined to be a data formation excluding range (see oblique line hatching lines) and stored.

Then, in the (ST6), since the visual field position [2] is located in a terminal end in the direction of Y, the procedure advances to (ST7) to determine the maximum value of the sizes of the data formation excluding ranges in the image pick-up visual fields in this column as an overlap margin in the direction of X. That is, the larger size of the width sizes BX2 and DX2 of the data formation excluding ranges in the direction of X in the visual fields in the visual field positions [1] and [2] is determined as the overlap margin in the direction of X upon change of a column position. Here, when the BX2 is larger than the DX2, the BX2 is determined as the overlap margin in the direction of X. Then, when the overlap margin in the direction of X is determined, the column position is changed (ST8).

Figure 12A:
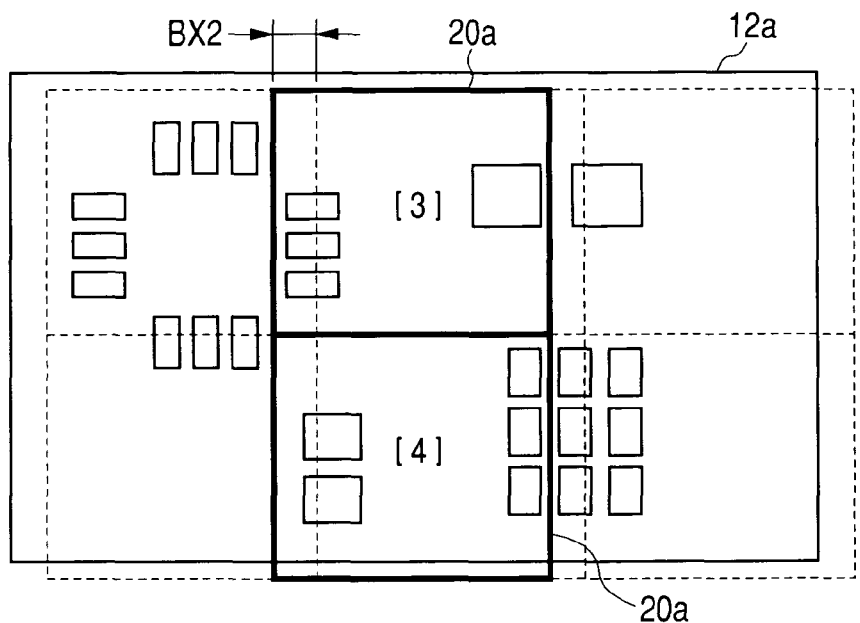
FIG. 12 is an explanatory view of the mask plate image pick-up process in the method for forming print inspecting data according to the first embodiment of the present invention.

As shown in FIG. 12(a), the image pick-up visual field 20a is moved to the visual field position [3] of a second column. At this time, the visual field 20a is not moved by a visual field size in the direction of X, and overlapped by the BX2 determined as the overlap margin in the direction of X on the image pick-up visual field in the visual field position of a first column. In other words, the overlap margin in the direction of X (second direction) in which two adjacent image pick-up visual fields are overlapped in the direction of X is set based on the maximum size of sizes of the incomplete opening parts in the direction of X detected in the first column movement. Then, in a column movement subsequent to the first column movement, the same overlap margin in the direction of X is used for all the visual field positions.

Figure 12B:
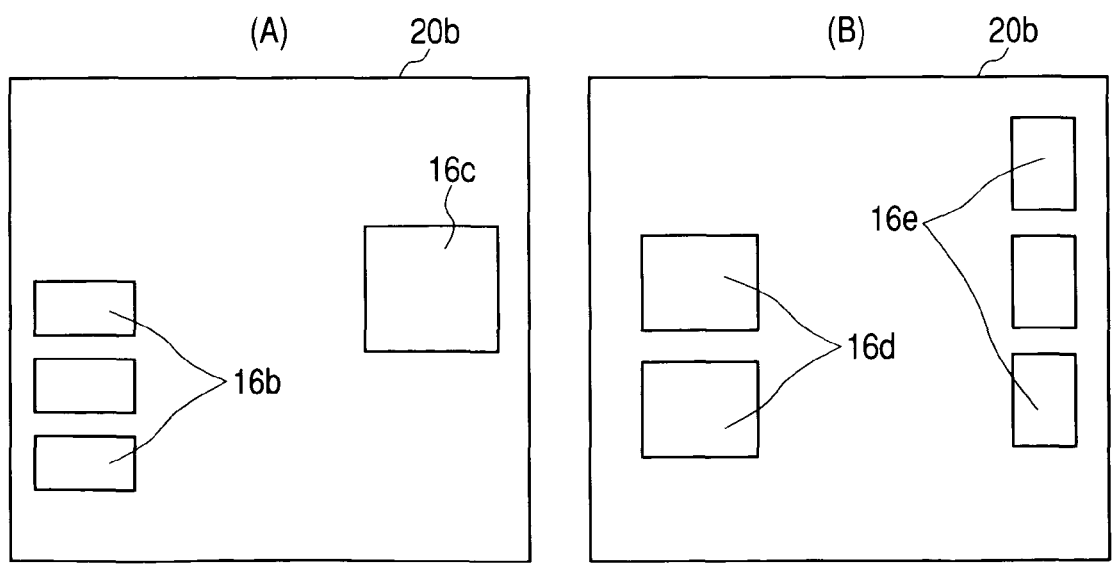

Thus, as shown in (A) of FIG. 12(b), the image 20b in which the pattern holes 16b, which are the incomplete opening parts on the image obtained in the visual field position [1], are completely included is obtained. Then, the same processes are performed for the image 20b. Here, since the incomplete opening parts are not detected in the image 20b, data formation excluding ranges are not set both in the directions of X and Y. Then, in the (ST11), after an overlap margin in the direction of Y is determined to be 0, the procedure returns to the (ST1) to move the image pick-up visual field.

In this case, the image pick-up visual field 20a is directly moved to the visual field position [4] shown in FIG. 12(a). Thus, as shown in (B) of FIG. 12(b), the image 20b in which pattern holes 16d, which are the incomplete opening parts on the image obtained in the visual field position [2], are completely included is obtained. Then, the same processes are performed for this image 20b.

Here, since the incomplete opening parts are not detected in the image 20b, data formation excluding ranges are not determined both in the directions of X and Y. Then, in the (ST6), since the visual field position [4] is located in a terminal end in the direction of Y, the procedure advances to the (ST7). However, since the incomplete opening parts are not detected in the second column, the procedure directly moves to the (ST8) to change a column position without overlapping in the direction of X. Then, after that, the same processes are repeated in the visual field positions [5] and [6]. Thus, the image pick-up processes for the mask plate 12 as an object are finished.

Specifically, in the above-described image pick-up processes, when the image pick-up visual field 20a of the camera 20 is sequentially moved to the plural visual field positions set to the mask plate 12 in a prescribed moving sequence to obtain a plurality of images, if the incomplete opening parts in which parts of the opening parts partly protrude from the image obtained in one image pick-up visual field and the forms are not completed are detected, the adjacent image pick-up visual field in the end of the image in which the incomplete opening parts are detected is overlapped by the overlap margin determined based on the size of the incomplete opening parts in the image on the one image pick-up visual field.

Accordingly, when the image pick-up visual field is moved on the mask plate to pick-up images a plurality of times, even if the opening parts may partly protrude from the image pick-up visual field in one visual field position, the opening parts are always completely included in any one of the images respectively on the obtained images. Therefore, the mask opening data can be simply and efficiently obtained to form the inspecting data without increasing a processing load or generating the deterioration of detection accuracy due to the fragmentation of the opening parts on the image.

As described above, according to the present invention in the first embodiment, in the mask data obtaining step for picking-up the image of the mask plate to obtain the positions or the forms of the opening parts, when the image pick-up visual field of the camera is sequentially moved to the plural visual field positions set to the mask plate in accordance with a prescribed moving sequence, if the incomplete opening parts which partly protrude from the image obtained in one image pick-up visual field are detected, the adjacent image pick-up visual field is overlapped by the overlap margin determined based on the size of the incomplete opening parts in the image on the one image pick-up visual field to pick-up the image. Thus, an inconvenience due to the protrusion of the opening parts in the obtained image can be eliminated and the inspecting data can be simply and efficiently formed.

(Second Embodiment)

In the present invention according to a second embodiment, in a mask data obtaining step for obtaining the forms or configurations and the positions of opening parts by picking-up the image of a mask plate, when the image pick-up visual field of a camera is sequentially moved to a plurality of visual field positions set to the mask plate in accordance with a prescribed moving sequence, if an incomplete opening part in which a part of the opening part partly protrudes from an image obtained in one image pick-up visual field, the incomplete opening part is registered as an opening part to be connected, and then, a connecting process is carried out in which an opening part to be connected that is already registered in an image obtained in an adjacent image pick-up visual field on an edge of an image where the opening part to be connected is detected and corresponds to the opening part to be connected is connected to the opening part to be connected to form one opening part. Thus, inspecting data can be simply and efficiently formed. The explanation of a part duplicated with the first embodiment will be omitted.

Figure 13:
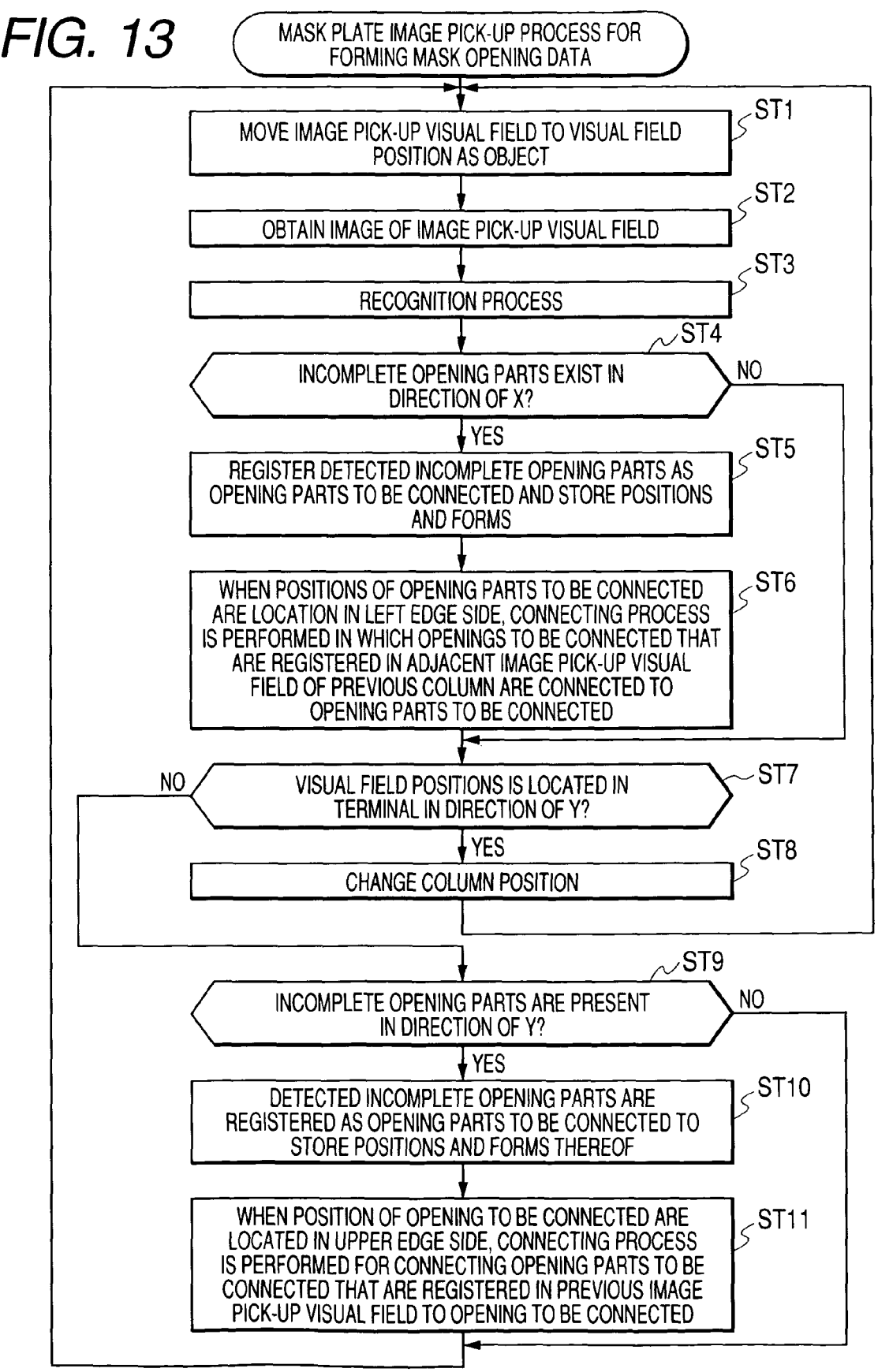
FIG. 13 is a flow chart for a mask plate image pick-up process for forming mask opening data in a method for forming print inspecting data according to a second embodiment of the present invention.

FIG. 13 is a flowchart of a mask plate image pick-up process for forming mask opening data in a method for forming printing inspection data according to the second embodiment of the present invention. FIGS. 14, 15 and 16 are explanatory views of the mask plate image pick-up process in the method for forming print inspecting data according to the second embodiment of the present invention.

Now, a specific image pick-up process will be described in accordance with the flow chart of FIG. 13. Firstly, a camera 20 is moved to the mask plate 12 to move an image pick-up visual field 20a to a target visual field position (ST1). Here, the first visual field position [1] shown in FIG. 9 is a first object whose image is to be picked-up. Then, the image of this image pick-up visual field is obtained by the camera 20 (ST2) to recognize the obtained image (ST3). Thus, an image 20b shown in FIG. 14(a) is obtained and pattern holes 16b in the image pick-up visual field are detected as the opening parts.

Here, it is decided whether or not the incomplete opening parts in which parts of the opening parts partly protrude from the image 20b so that their forms are not completed are detected in the direction of X (ST4). Then, when the incomplete opening parts are present in the direction of X, the detected incomplete opening parts are registered as opening parts to be connected in the image to store the positions and forms thereof (ST5).

Figure 14A:
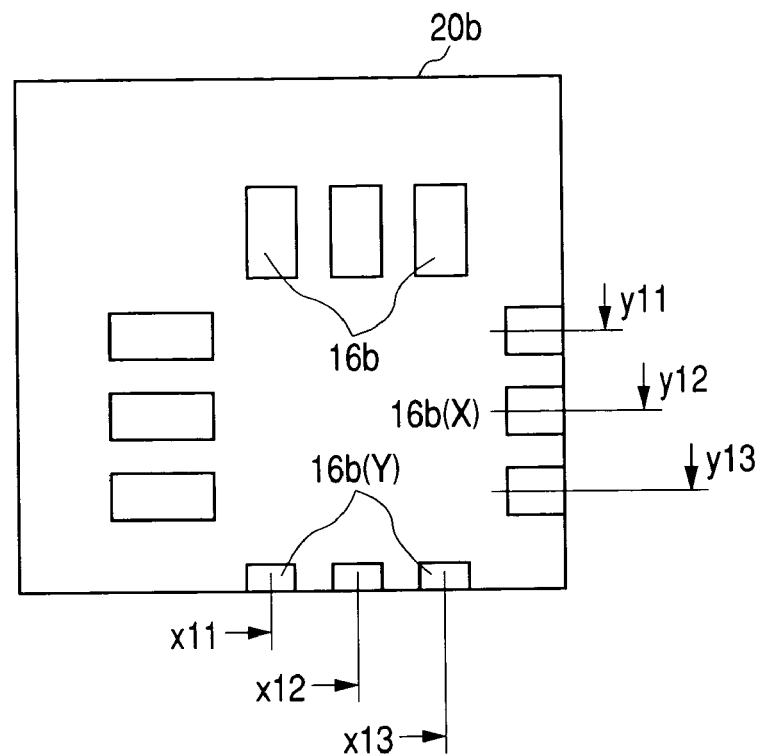
FIG. 14 is an explanatory view of the mask plate image pick-up process in the method for forming print inspecting data according to the second embodiment of the present invention.

Specifically, in this example, as shown in FIG. 14(a), the incomplete opening parts 16b (X) corresponding to the pattern holes 16b are detected in the right boundary side in the image 20b. Then, the forms of the incomplete opening parts 16b (X) (here, rectangular shapes) are decided and y11, y12 and y13 as positions in the direction of Y are obtained on the image to store these data.

Here, the positions of opening parts to be connected are located in a left side in the visual field, a process is carried out for connecting opening parts to be connected which are already registered in an adjacent image pick-up visual field of a previous column to the opening parts to be connected which are registered in the image of the image pick-up visual field. In this example, since the visual field position [1] is in a first column, the previous column does not exist. Accordingly, the connecting process is not performed.

Then, whether or not the visual field position is located in a terminal end of the direction of Y (ST7). Since the visual field position [1] does not exist in the terminal end of the direction of Y, the procedure advances to (ST9) to decide whether or not incomplete opening parts exist in the direction of Y. Then, when the incomplete opening parts are present in the direction of Y, the detected incomplete opening parts are registered as opening parts to be connected to store the positions and forms thereof (ST10).

Specifically, as shown in FIG. 14(a), the incomplete opening parts 16b (Y) corresponding to the pattern holes 16b are detected in the lower side in the image 20b. Then, the configurations of the incomplete opening parts 16b (Y) are decided and positions x11, x12 and x13 in the direction of X are obtained on the image to store these data.

Here, when the positions of opening parts to be connected are located in an upper edge side in a visual field, a connecting process is carried out in which opening parts to be connected that are already registered in a previous image pick-up visual field are connected to the opening parts to be connected that are registered in the image of this image pick-up visual field. In the example shown in FIG. 14(a), since the incomplete opening parts 16b (Y) are detected only in the lower edge side, the connecting process is not carried out.

Figure 14B:
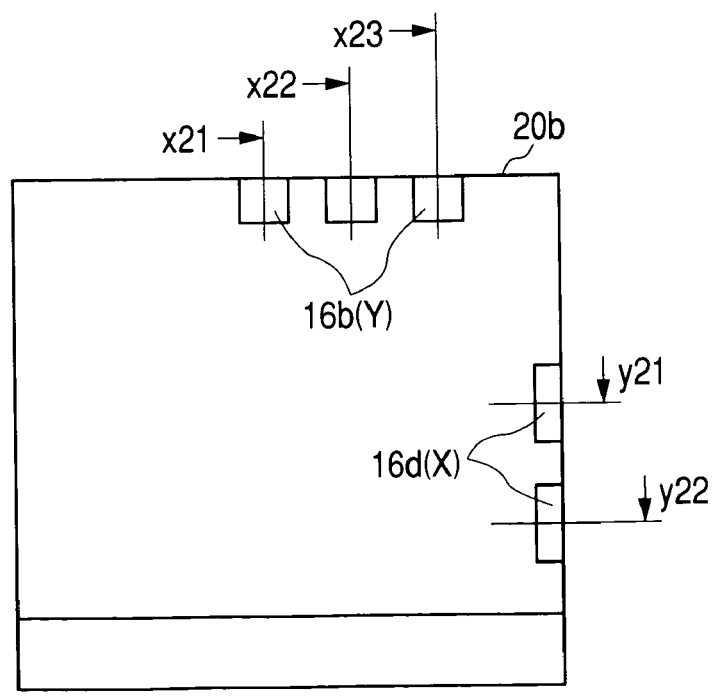

After that, the procedure returns to the (ST1) to move the image pick-up visual field 20a to the visual field [2] as a next object and repeat the steps after the (ST2). Thus, an image shown in FIG. 14(b) is obtained and incomplete opening parts 16d (X) in the direction of X are detected in a right edge side and incomplete opening parts 16b (Y) in the direction of Y are detected in an upper edge side. Then, these incomplete opening parts 16d (X) and 16b (Y) are registered as opening parts to be connected to store respectively the configurations or forms and positions x21, x22, x23, y21 and y22 thereof.

Figure 15A:
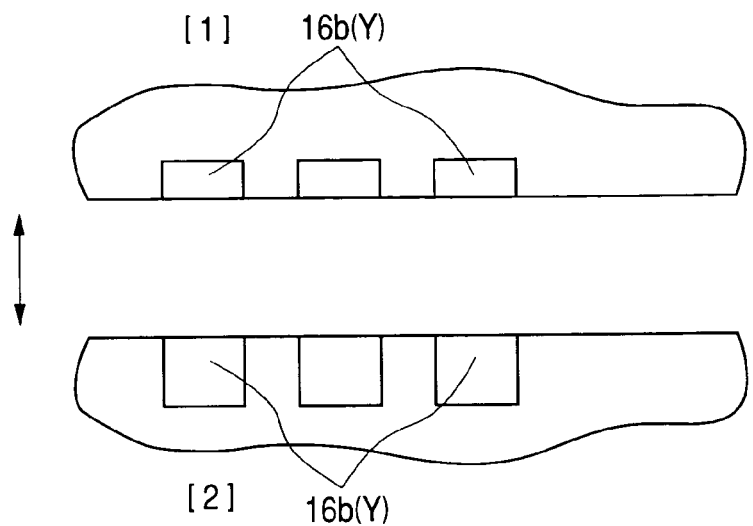
FIG. 15 is an explanatory view of the mask plate image pick-up process in the method for forming print inspecting data according to the second embodiment of the present invention.

Since the incomplete opening parts 16b (Y) in the direction of Y are detected in the upper edge side, a connecting process is performed in (ST11) in which the incomplete opening parts 16b (Y) are connected to the opening parts to be connected that are already registered in the previous image pick-up visual field. That is, as shown in FIG. 15(a), the incomplete opening parts 16b (Y) included in the image in the visual field position [1] are butted and connected onto the incomplete opening parts 16b (Y) included in the image in the image pick-up visual field [2].

Figure 15B:
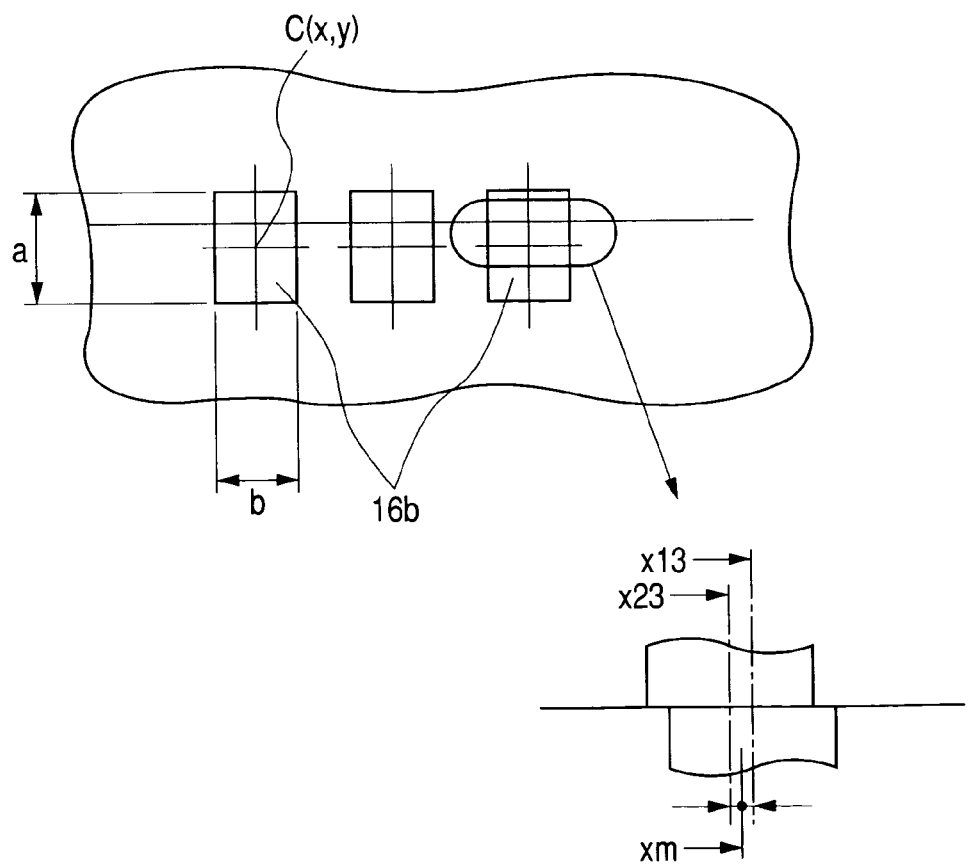

Accordingly, as shown in FIG. 15(b), the two incomplete opening parts obtained in the separate images are connected together to form the opening parts 16b (pattern holes) whose configurations are completed on the image. Then, on the basis of this image, data showing sizes a and b and a central position C (x, y) of each opening part 16 is obtained which have been incapable of being detected in the original images obtained by picking-up the images respectively in the visual fields. Then, the data of the opening parts in which these connecting processes are performed is combined with the data of the opening parts individually detected in the respective images to obtain the mask opening data shown in FIG. 7.

When the two images are butted on each other in the connecting process, the central positions of the incomplete opening parts do not usually correspond to each other. As shown in one opening part 16b of FIG. 15(b), the positions x13 and x23 in the direction of X do not sometimes correspond to each other. In such a case, the average position xm of the positions x13 and x23 is obtained as a central point of dislocation and the two incomplete opening parts are respectively moved to the central point of dislocation. That is, in this connecting process, when the opening part to be connected is dislocated from the opening part to be connected that corresponds thereto and is already registered, both the opening parts are respectively moved by half an amount of dislocation toward the central point of dislocation.

Figure 16A:
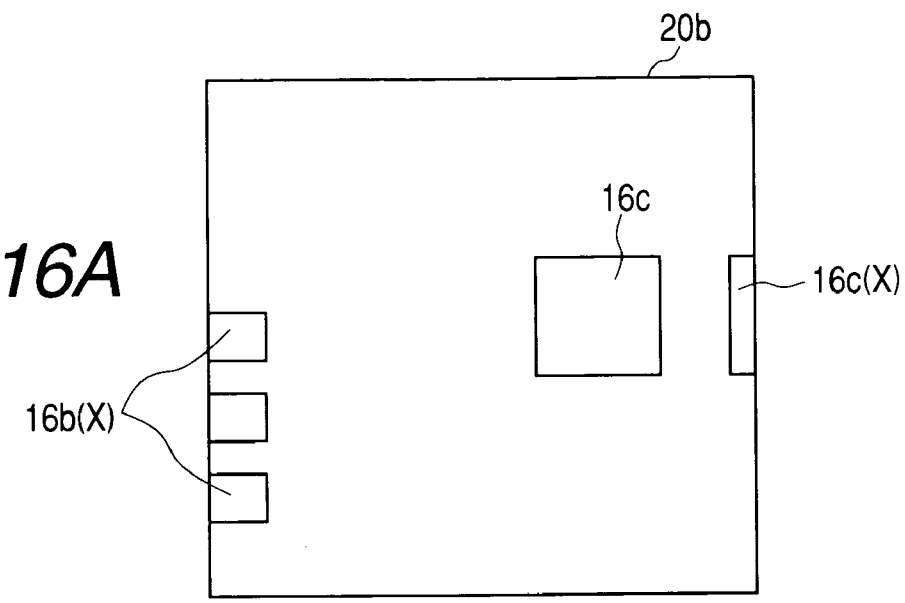
FIG. 16 is an explanatory view of the mask plate image pick-up process in the method for forming print inspecting data according to the second embodiment of the present invention.
Figure 16B:
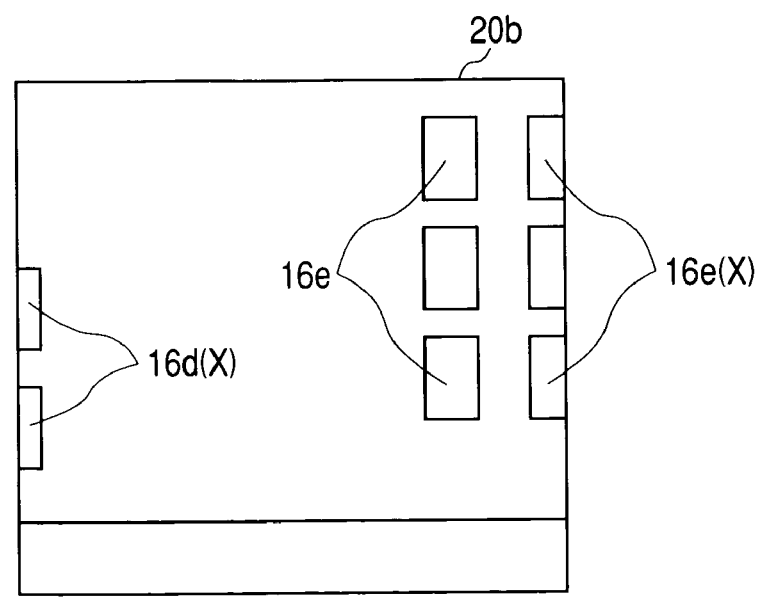

After that, the procedure returns again to the (ST1) to move the image pick-up visual field 20a to a visual field position as a next object and repeat the same processes. Thus, in the visual field positions [3] and [4], images shown in FIGS. 16(a) and 16(b) are obtained. Then, a connecting process is carried out in which the opening parts 16b (X) to be connected in the direction of X that are already detected and registered in the visual field position [1] are butted and connected to the opening parts 16b (X) to be connected in the direction of X are detected and registered in the visual field position [3]. Further, a connecting process is carried out in which the opening parts 16d (X) to be connected in the direction of X that are already detected and registered in the visual field position [2] are butted and connected onto the opening parts 16d (X) to be connected in the direction of X that are detected and registered in the visual field position [4]. Then, after that, the same image pick-up processes are performed in the visual field positions [5] and [6], so that the image pick-up processes for the mask plate 12 as a target are completed.

That is, in the above-described image pick-up processes, when the image pick-up visual field 20a of the camera 20 is sequentially moved to a plurality of visual field positions set to the mask plate 12 in a prescribed moving sequence, if the incomplete opening parts in which parts of the opening parts partly protrude from the image obtained in one image pick-up visual field so that the forms are not completed are detected, the incomplete opening parts are registered as the opening parts to be connected in this image. Then, a connecting process is carried out in which the opening parts to be connected that are already registered in the image obtained in the adjacent image pick-up visual filed in the edge of the image in which the opening parts to be connected are detected and correspond to the opening parts to be connected are searched, and the opening parts to be connected that are already registered are connected to the opening parts to be connected to form complete openings respectively.

Thus, when the image pick-up visual field is moved on the mask plate to pick-up the images a plurality of times, even if the opening parts may possibly partly protrude from the image pick-up visual field in one visual field position, the corresponding incomplete opening parts are properly butted and connected onto the above-described opening parts. Consequently, the positions and forms of the opening parts can be precisely obtained so that the mask opening data can be simply and efficiently obtained to form the inspecting data.

As described above, according to the present invention of the second embodiment, in the mask data obtaining step for obtaining the positions or the configurations of the opening parts by picking-up the image of the mask plate, when the image pick-up visual field of the camera is sequentially moved to a plurality of visual field positions set to the mask plate in a prescribed moving sequence, if the incomplete opening parts partly protruding from the image obtained in one image pick-up visual field are detected, the incomplete opening parts are registered as the opening parts to be connected in this image, and then, a connecting process is carried out in which the opening parts to be connected that are already registered in the image obtained in the adjacent image pick-up visual filed in the edge of the image in which the opening parts to be connected are detected and correspond to the opening parts to be connected are connected to the opening parts to be connected to form complete openings respectively. Accordingly, the inspecting data can be simply and efficiently formed.

As described above, according to the present invention, in the mask data obtaining step for obtaining the positions or the configurations of the opening parts by picking-up the image of the mask plate, when the image pick-up visual field of the camera is sequentially moved to a plurality of visual field positions set to the mask plate in a prescribed moving sequence, if the incomplete opening parts partly protruding from the image obtained in one image pick-up visual field are detected, a process for obtaining the complete opening parts to which the incomplete opening parts belong is performed based on the detected result. Therefore, the inspecting data can be simply and efficiently formed.

What is claimed is:

1. A method for forming printing inspection data which is used in a printing inspection apparatus for inspecting the printed state of the cream solder of a board after a screen printing to form the inspecting data including configuration and position data showing the configurations and positions of solder printing parts in which the cream solder is printed on a printing surface, wherein, in a mask data obtaining step for obtaining element configuration and position data showing the configurations and the positions of the element solder printing parts printed on electrodes for connecting together electronic parts provided on the circuit forming surface of the board by detecting opening parts of a mask plate on the basis of images obtained by picking-up the images of the mask plate used for the screen printing by a camera, when the image pick-up visual field of the camera is sequentially moved to a plurality of visual field positions set to the mask plate in accordance with a prescribed moving sequence to obtain a plurality of images, if an incomplete opening part in which a part of the opening part partly protrudes so that a configuration is not completed is detected from an image obtained in one image pick-up visual field, a process for obtaining data of a complete opening part to which the incomplete opening part belongs is carried out in accordance with the detected result.

2. A method for forming printing inspection data which is used in a printing inspection apparatus for inspecting the printed state of the cream solder of a board after a screen printing to form the inspecting data including configuration and position data showing the configurations and positions of solder printing parts in which the cream solder is printed on a printing surface, wherein, in a mask data obtaining step for obtaining element configuration and position data showing the configurations and the positions of element solder printing parts printed on electrodes for connecting together electronic parts provided on the circuit forming surface of the board by detecting opening parts of a mask plate on the basis of images obtained by picking-up the images of the mask plate used for the screen printing by a camera, when the image pick-up visual field of the camera is sequentially moved to a plurality of visual field positions set to the mask plate in accordance with a prescribed moving sequence to obtain a plurality of images, if an incomplete opening part in which a part of the opening part partly protrudes so that a configuration is not completed is detected from an image obtained in one image pick-up visual field, an adjacent image pick-up visual field in the end of the image in which the incomplete opening part is detected is overlapped on the one image pick-up visual field by an overlap margin determined by the size of the incomplete opening part in the image.

3. A method for forming printing inspection data according to claim 2, wherein the plural visual field positions are set in a substantially grid shaped arrangement and the prescribed moving sequence is a moving sequence performed in such a manner that a liner column movement toward the same direction from a start end to a terminal end in a first direction in the grid shaped arrangement is repeated in a second direction perpendicular to the first direction.

4. A method for forming printing inspection data according to claim 3, wherein the overlap margin in the second direction of the overlap margins in which two adjacent image visual fields are overlapped in the second direction is set on the basis of a maximum size of sizes of the incomplete opening parts in the second direction which are detected in the first column movement and the same overlap margin in the second direction is used in a column movement subsequent to the first column movement.

5. A method for forming printing inspection data which is used in a printing inspection apparatus for inspecting the printed state of the cream solder of a board after a screen printing to form the inspecting data including configuration and position data showing the configurations and positions of solder printing parts in which the cream solder is printed on a printing surface, wherein, in a mask data obtaining step for obtaining element configuration and position data showing the configurations and the positions of element solder printing parts printed on electrodes for connecting together electronic parts provided on the circuit forming surface of the board by detecting opening parts of a mask plate on the basis of images obtained by picking-up the image of the mask plate used for the screen printing by a camera, when the image pick-up visual field of the camera is sequentially moved to a plurality of visual field positions set to the mask plate in accordance with a prescribed moving sequence to obtain a plurality of images, if an incomplete opening part in which a part of the opening part partly protrudes so that a configuration is not completed is detected from an image obtained in one image pick-up visual field, the incomplete opening part is registered as an opening part to be connected in the image, and then, a connecting process is carried out in which an opening part to be connected that is already registered in an image obtained in an adjacent image pick-up visual field on the edge of the image edge where the opening part to be connected is detected and corresponds to the opening part to be connected is connected to the opening part to be connected to form one opening part.

6. A method for forming printing inspection data according to claim 5, wherein the plural visual field positions are set in a substantially grid shaped arrangement and the prescribed moving sequence is a moving sequence performed in such a manner that a liner column movement toward the same direction from a start end to a terminal end in a first direction in the grid shaped arrangement is repeated in a second direction perpendicular to the first direction.

7. A method for forming printing inspection data according to claim 6, wherein when the opening part to be connected is dislocated from the already-registered opening part to be connected in the connecting process, both the opening parts are respectively moved by half an amount of dislocation toward the central point of dislocation.

* * * * *